(12) United States Patent
Soin et al.

(10) Patent No.: US 11,247,902 B2
(45) Date of Patent: Feb. 15, 2022

(54) PHARMACEUTICAL FORMULATIONS OF NITRITE AND USES THEREOF

(71) Applicant: Board of Supervisors of Louisiana State University and Agricultural and Mechanical College, Baton Rouge, LA (US)

(72) Inventors: Amol Soin, Centerville, OH (US); Christopher Kevil, Shreveport, LA (US); Kyle Chan, San Diego, CA (US); Anthony Giordano, Chesterland, OH (US)

( * ) Notice: Subject to any disclaimer, the term of this patent is extended or adjusted under 35 U.S.C. 154(b) by 93 days.

(21) Appl. No.: 16/307,739

(22) PCT Filed: Jun. 6, 2017

(86) PCT No.: PCT/US2017/036166
§ 371 (c)(1),
(2) Date: Dec. 6, 2018

(87) PCT Pub. No.: WO2017/214157
PCT Pub. Date: Dec. 14, 2017

(65) Prior Publication Data
US 2020/0121714 A1    Apr. 23, 2020

Related U.S. Application Data

(60) Provisional application No. 62/346,359, filed on Jun. 6, 2016.

(51) Int. Cl.
| | | |
|---|---|---|
| *A61P 25/02* | (2006.01) | |
| *C01B 21/50* | (2006.01) | |
| *A61K 31/381* | (2006.01) | |
| *A61K 31/095* | (2006.01) | |
| *A61K 31/137* | (2006.01) | |
| *A61K 31/445* | (2006.01) | |
| *A61K 33/00* | (2006.01) | |

(52) U.S. Cl.
CPC ............ *C01B 21/50* (2013.01); *A61K 31/095* (2013.01); *A61K 31/137* (2013.01); *A61K 31/381* (2013.01); *A61K 31/445* (2013.01); *A61K 33/00* (2013.01); *A61P 25/02* (2018.01)

(58) Field of Classification Search
None
See application file for complete search history.

(56) References Cited

U.S. PATENT DOCUMENTS

| | | | |
|---|---|---|---|
| 2011/0086069 A1 | 4/2011 | Kevil et al. | |
| 2015/0196588 A1 | 7/2015 | Kevil et al. | |
| 2017/0349438 A1* | 12/2017 | Soin ................ | A61K 31/381 |

FOREIGN PATENT DOCUMENTS

| | | |
|---|---|---|
| CN | 102309575 A | 1/2012 |
| CN | 102309575 B | 4/2013 |

OTHER PUBLICATIONS

Navera (Dayton Business Journal, Feb. 4, 2015, www.soinneuroscience.com/2015/02/19/dayton-area-entrepreneur-on-cusp-of-billion-dollar-product-exclusive/).*
Cameron (Diabetologia (1994) 37:449-459).*
DeVan (FASEB Journal, vol. 28, No. 1 supplement, Apr. 2014).*
Bir (Diabetes vol. 63, Jan. 2014, pp. 270-281).*
Behse (Journal of Neurology, Neurosurgery, and Psychiatry, 1977, 40, 1072-1082).*
Soin (New Diabetic Pain Drug Tested in Dayton, interview on Fox 45, https://www.youtube.com/watch?time_continue=97&v=3mlUAtbim5s&feature=emb_logo, uploaded Mar. 6, 2015, accessed May 26, 2020).*
International Search Report issued in corresponding International Patent Application No. PCT/US2017/036166 dated Aug. 14, 2017.
International Search Report Corresponding to PCT/US2017/036166 dated Aug. 14, 2017.
Written Opinion Corresponding to PCT/US2017/036166 dated Aug. 14, 2017.

\* cited by examiner

*Primary Examiner* — Robert T. Crow
*Assistant Examiner* — John P Nguyen
(74) *Attorney, Agent, or Firm* — Holoubek Patent Law, LLC; Charlotte Holoubek

(57) ABSTRACT

The present invention relates to pharmaceutical compositions of nitrites such as inorganic nitrites, or any pharmaceutically acceptable salts, solvates, or prodrugs thereof, and the medical use of these compositions. The pharmaceutical compositions, which can be formulated for oral administration, can provide immediate release or extended release of the nitrite ion ($NO_2^-$). The pharmaceutical compositions of the invention are useful, for example, for treating or reducing pain, improving symptoms of a microvascular disease, and improving nerve conduction velocity.

20 Claims, 4 Drawing Sheets

US 11,247,902 B2

PHARMACEUTICAL FORMULATIONS OF NITRITE AND USES THEREOF

FIELD OF THE INVENTION

The invention features pharmaceutical compositions of nitrites and methods using these compositions to treat or reduce pain and symptoms of microvascular disease.

BACKGROUND

Nitric oxide (NO) is involved in many physiological processes and plays a key role in redox signaling. In particular, endothelial-derived NO regulates normal vascular function by stimulating NO-dependent activation of soluble guanylate cyclase, which leads to the activation of a signaling cascade resulting in smooth muscle relaxation and vasodilation. Dysfunction in NO-dependent signaling processes can occur either through a deficit in NO synthesis, NO bioavailability, or both. For instance, studies have shown that endothelial-derived NO production is reduced in patients with peripheral artery disease. Thus, reduced NO bioavailability might substantially contribute to the development of microvascular disease.

Studies have also indicated that NO plays a complex and diverse role in the incidence of pain. For instance, NO is an essential neurotransmitter involved in the nociceptive process and contributes to central sensitization in the dorsal horn of the spinal cord. In contrast, other studies have implicated that NO can inhibit nociception in the central and peripheral nervous system. NO has also been shown to mediate the analgesic effect of opioids, such as morphine.

Accordingly, there exists a need in the medical field to develop safe and effective treatments that restore NO bioavailability in patients with microvascular disease and that provide a source of NO to mitigate pain. Thus, therapeutic strategies that modulate NO are highly desirable.

SUMMARY OF THE INVENTION

The invention features methods to treat or reduce pain in a patient (such as a mammal (e.g., a human)) by administering sodium nitrite or a pharmaceutically acceptably salt thereof. Additionally, methods of treating a microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans) by administering sodium nitrite or a pharmaceutically acceptably salt thereof to a patient are disclosed. The methods feature a first step of administering a low dose (e.g., about 5 mg to about 50 mg twice daily) of inorganic nitrite to the patient to, e.g., treat or reduce pain. The methods feature a second step of administering a high dose (e.g., about 60 mg to about 100 mg twice daily) of inorganic nitrite to the patient to, e.g., treat symptoms of microvascular disease. The invention also feature methods of improving nerve conduction velocity in a patient (e.g., a patient identified as being in need of improved nerve conduction velocity) by administering a high dose (e.g., about 60 mg to about 100 mg (e.g., 80 mg) twice daily) of inorganic nitrite to the patient to increase nerve conduction velocity.

A first aspect of the invention features a method of treating or reducing pain, such as chronic pain, in a patient (such as a mammal (e.g., a human)). The method of the first aspect includes: (i) administering about 5 mg to about 50 mg of inorganic nitrite or a pharmaceutically acceptable salt thereof (e.g., 40 mg of inorganic nitrite or a pharmaceutically acceptable salt thereof) to the patient two times per day for a first treatment period of 6 weeks to 14 weeks (e.g., at least 7 weeks, at least 8 weeks, at least 9 weeks, at least 10 weeks, at least 11 weeks, at least 12 weeks, or at least 13 weeks); and then (ii) administering about 60 mg to about 100 mg of inorganic nitrite or a pharmaceutically acceptable salt thereof (e.g., 80 mg of inorganic nitrite or a pharmaceutically acceptable salt thereof) to the patient two times per day for a second treatment period of 6 weeks to 14 weeks (e.g., at least 7 weeks, at least 8 weeks, at least 9 weeks, at least 10 weeks, at least 11 weeks, at least 12 weeks, or at least 13 weeks). Preferably, the first treatment period is at least 10 weeks.

In some embodiments, the pain is neuropathic pain, inflammatory pain, nociceptive pain, functional pain, musculo-skeletal pain, or central nervous system pain. In some embodiments, the neuropathic pain is diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome.

Additionally, in some embodiments, the patient can have a microvascular disease, such as peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans. In some embodiments, the patient can also have type 1 diabetes or type 2 diabetes.

A second aspect of the invention features a method of treating a microvascular disease in a patient (such as a mammal (e.g., a human)). For example, the microvascular disease is peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans. In some embodiments, the patient can have type 1 diabetes or type 2 diabetes.

The method of the second aspect includes the steps of: (i) administering about 5 mg to about 50 mg of inorganic nitrite or a pharmaceutically acceptable salt thereof (e.g., 40 mg of inorganic nitrite or a pharmaceutically acceptable salt thereof) to the patient two times per day for a first treatment period of 6 weeks to 14 weeks (e.g., at least 7 weeks, at least 8 weeks, at least 9 weeks, at least 10 weeks, at least 11 weeks, at least 12 weeks, or at least 13 weeks); and then (ii) administering about 60 mg to about 100 mg (e.g., 80 mg of inorganic nitrite or a pharmaceutically acceptable salt thereof) of inorganic nitrite or a pharmaceutically acceptable salt thereof to the patient two times per day for a second treatment period of 6 weeks to 14 weeks (e.g., at least 7 weeks, at least 8 weeks, at least 9 weeks, at least 10 weeks, at least 11 weeks, at least 12 weeks, or at least 13 weeks). Preferably, the first treatment period is at least 10 weeks.

The method can optionally further include determining whether the patient, such as a patient with chronic pain, exhibits a reduction in pain. In some embodiments, the reduction in pain is determined as a decrease in pain intensity, frequency, duration, and/or improvements in quality of life. For example, the method can optionally include performing a Brief Pain Inventory, a Neuropathic Pain Symptom Inventory, and/or a McGill Pain Questionnaire to determine if the patient exhibits a reduction in pain. Desirably, step (i) of the method results in a reduction in pain. In some embodiments, step (ii) is performed when the patient exhibits a reduction in pain.

The method can also include the optional step of determining whether the patient (such as a mammal (e.g., a human)) experiences an improvement in one or more symptoms of the microvascular disease, e.g., in which the improvement in one or more symptoms of the microvascular disease is determined as an increase in nitric oxide availability, physical function, and/or motor neuron activity. For example, the method can optionally include performing flow-mediated dilation to determine nitric oxide availability, a RAND-36 Questionnaire to determine physical function, and/or an assessment of nerve conduction velocity to determine motor neuron activity. Preferably, step (ii) of the method results in an improvement in one or more symptoms of the microvascular disease.

A third aspect of the invention features a method of improving nerve conduction velocity in a patient (e.g., a mammal, such as a human) identified as being in need of improved nerve conduction velocity. The method of the third aspect includes administering about 60 mg to about 100 mg of inorganic nitrite or a pharmaceutically acceptable salt thereof twice daily (e.g., about 70 mg to about 90 mg twice daily, such as about 70 mg, about 75 mg, or about 80 mg twice daily) to the patient for a treatment period (e.g, at least 6 weeks, at least 7 weeks, at least 8 weeks, at least 9 weeks, at least 10 weeks, at least 11 weeks, at least 12 weeks, at least 13 weeks, or at least 14 weeks or longer) sufficient to improve nerve conduction velocity in the patient.

In some embodiments, the method of the third aspect further includes monitoring whether there is an increase in nerve conduction velocity in the patient (e.g., a mammal, such as a human), such as by performing a nerve conduction velocity test and/or a sensory test to assess the patient's ability to feel, e.g., pain. For example, there is an increase in nerve conduction velocity after administration of the inorganic nitrite or the pharmaceutically acceptable salt (e.g., an increase in nerve conduction velocity of about 1 m/s, about 1.5 m/s, about 2 m/s, about 2.5 m/s, about 3 m/s, about 3.5 m/s, about 4 m/s, about 4.5 m/s, about 5 m/s, about 5.5 m/s, about 6 m/s, or about 6.5 m/s or more) relative to the nerve conduction velocity of the patient prior to administration of the inorganic nitrite or the pharmaceutically acceptable salt. In some embodiments, a sensory test may be performed using, e.g., a monofilament, placed on the patient's skin, such as on the patient's feet, to assess the nerve conduction velocity of the patient. For example, the patient exhibits an increased ability to sense the monofilament after administration of the inorganic nitrite (e.g., about 60 mg to about 100 mg of inorganic nitrite twice daily, such as about 80 mg twice daily) relative to the ability of the patient to sense the monofilament prior to administration of the inorganic nitrite.

In some embodiments, the patient (e.g., a mammal, such as a human) has a microvascular disease, such as diabetic neuropathy, peripheral artery disease, scleroderma, Raynaud's disease, cerebral autosomal dominant arteriopathy with sub-cortical infarcts and leukoencephalopathy, thrombotic microangiopathy, or thromboangiitis obliterans. For example, the method of the third aspect further includes determining whether the patient experiences an improvement in one or more symptoms of the microvascular disease, e.g., in which the improvement in one or more symptoms of the microvascular disease is determined as an increase in nitric oxide availability or physical function. In preferred embodiments, the patient experiences an improvement in one or more symptoms of the microvascular disease after administration of the inorganic nitrite or the pharmaceutically acceptable salt. Additionally, in some embodiments, the patient does not have pain associated with the microvascular disease.

In any of the above aspects, the inorganic nitrite can be, e.g., $NaNO_2$, $KNO_2$, or $Ca(NO_2)_2$. Preferably, the inorganic nitrite is $NaNO_2$. For example, the inorganic nitrite or the pharmaceutically acceptable salt thereof can be formulated, e.g., for topical, enteral, or parenteral administration and/or as a solid dosage form for oral administration. In some embodiments, the inorganic nitrite or the pharmaceutically acceptable salt thereof is formulated as a tablet or capsule, such as for sustained release of the inorganic nitrite. In some embodiments, the inorganic nitrite or the pharmaceutically acceptable salt thereof can be formulated with one or more pharmaceutically acceptable excipients.

Definitions

As used herein, "a" or "an" means "at least one" or "one or more" unless otherwise indicated. In addition, the singular forms "a," "an," and "the" include plural referents unless the context clearly dictates otherwise. Thus, for example, reference to a composition containing "a therapeutic agent" includes a mixture of two or more therapeutic agents.

As used herein, "about" refers to an amount that is ±10% of the recited value and is preferably ±5% of the recited value, or more preferably ±2% of the recited value.

As used herein, "at least" refers to an amount that is ≤10% of the recited value and is preferably ≤5% of the recited value, or more preferably ≤2% of the recited value.

By "chronic pain" is meant pain that lasts longer than three to six months or pain that extend beyond the expected period of healing. Chronic pain may originate with an initial trauma/injury or infection, or may be an ongoing cause of pain associated with neuropathic pain (e.g., diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome), headaches, joint pain, backaches, sinus pain, muscle pain, nerve pain, and pain affecting specific parts of the body, such as shoulders, pelvis, and neck. Chronic pain may also be associated with lower back pain, arthritis, headache, multiple sclerosis, fibromyalgia, shingles, nerve damage, or cancer.

As used interchangeably herein, the terms "decreasing" and "reducing" refer to the ability to cause an overall decrease preferably of 20% or greater, more preferably of 50% or greater, and most preferably of 75%, 85%, 90%, 95%, or greater. In particular, decreasing or reducing can refer to treatment that alleviates one or more symptoms of a disease, disorder, or conditions described herein (e.g., a microvascular disorder or pain).

As used herein, the term "delayed release" refers to a pharmaceutical preparation, e.g., an orally administered formulation of inorganic nitrite, which passes through the stomach substantially intact and dissolves in the small and/or large intestine (e.g., the colon). For instance, delayed release of the active agent (e.g., inorganic nitrite as described herein) results from the use of an enteric coating of an oral medication (e.g., an oral dosage form).

The term an "effective amount" of an agent, such as inorganic nitrite, is the amount sufficient to effect beneficial or desired results, such as clinical results, and, as such, an "effective amount" depends upon the context in which it is being applied.

The terms "extended release" or "sustained release" interchangeably refer to a drug formulation that provides for gradual release of a drug (e.g., inorganic nitrite) over an extended period of time, e.g., 6-12 hours or more, compared to an immediate release formulation of the same drug. Preferably, although not necessarily, the formulation results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the term "microvascular disease" refers to diseases or disorders of small, resistance vessels (e.g., pre-capillary arterioles) with an internal diameter of less than 100 microns, which can be caused by metabolic or oxidative stress leading to microvascular dysfunction and/or damage. For example, microvascular disease includes, but is not limited to, peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans.

As used herein, the term "monofilament" refers to a plastic fiber used by, e.g., a physician, to assess a patient's ability to sense pressure on their extremities, such as the feet, in a monofilament test. The monofilament test, for example, is administered to a patient to assess the nerve conduction velocity of the patient and/or to determine if the patient has a disorder associated with decreased nerve conduction velocity (e.g., a microvascular disease, such as diabetic neuropathy). The bent monofilament may exert a pressure of, e.g., 10 grams, on the patient's foot. During a monofilament test, the bent or unbent monofilament is touched to different points on the sole of the patient's foot. The patient will then identify when they sense the monofilament. If the patient is unable to sense the bent monofilament, e.g., exerting a pressure of 10 grams on the patient's foot, then the patient is characterized as being in need of improved nerve conduction velocity and/or may have a microvascular disease, such as diabetic neuropathy, peripheral artery disease, scleroderma, Raynaud's disease, cerebral autosomal dominant arteriopathy with sub-cortical infarcts and leukoencephalopathy, thrombotic microangiopathy, or thromboangiitis obliterans. The monofilament test allows for the identification of patients in need of improved nerve conduction velocity and the monitoring of patients for improvements in nerve conduction velocity after administration of inorganic nitrite as described herein.

As used herein, the term "neuropathic pain" refers to pain caused by damage or disease affecting the somatosensory nervous system. For example, neuropathic pain includes, but is not limited to, diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome, headaches, joint pain, backaches, sinus pain, muscle pain, nerve pain, and pain affecting specific parts of the body, such as shoulders, pelvis, and neck, and/or pain that is associated with lower back pain, arthritis, headache, multiple sclerosis, fibromyalgia, shingles, nerve damage, or cancer.

As used herein, the term "nerve conduction velocity" refers to the speed of one or more electrochemical signals across a neural pathway. Measurements of nerve conduction velocity serve as an indicator of nerve health in patients. For example, nerve conduction velocity tests may be performed by, e.g., attaching two electrode's to a patient's skin over a test nerve, administering an electrical impulse through one electrode to stimulate the nerve, recording the electrical impulse through the nerve at the second electrode, and determining the time difference between stimulation from the first to second electrode (e.g., in m/s). Nerve conduction velocity tests may also be performed using a multi-electrode array (e.g., a 3-dimensional electrode array).

As used herein, "prevention" refers to a prophylactic treatment, such as inorganic nitrite, given to a subject who has or will have a disease, a disorder, a condition (e.g., pain), or one or more symptoms associated with a disease, a disorder, or a condition (e.g., symptoms associated with microvascular disease).

The term "pharmaceutical composition," as used herein, represents a composition containing a compound described herein (e.g., inorganic nitrite, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers to any ingredient other than the compounds described herein (for example, a vehicle capable of suspending or dissolving the active compound) and having the properties of being nontoxic and non-inflammatory in a patient. Excipients may include, for example, antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to, butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, or ethylamine.

As used interchangeably herein, the terms "subject" and "patient" refer to any animal (such as a mammal, e.g., a human). A subject to be treated or tested for responsiveness to a therapy according to the methods described herein can be one who has been diagnosed with pain and/or a microvascular disease.

As used herein, "treating" refers to administering a pharmaceutical composition, such as inorganic nitrite, for prophylactic and/or therapeutic purposes. To "reduce the likelihood" refers to prophylactic treatment of a patient who is not yet ill, but who is susceptible to, or otherwise at risk of, a particular disease or condition (e.g., the conditions described herein, such as pain and/or microvascular disease). To "treat disease" or use for "therapeutic treatment" refers to administering treatment to a patient already suffering from a disease to ameliorate the disease and improve the patient's condition. The term "treating" also includes treating a patient to delay progression of a disease or its symptoms. Beneficial or desired results can include, but are not limited to, alleviation, amelioration, or prevention of pain and/or microvascular disease, a condition associated with pain and/or microvascular disease, or one or more symptoms associated with pain and/or microvascular disease.

The term "unit dosage forms" refers to physically discrete units suitable as unitary dosages for human subjects and other mammals, each unit containing a predetermined quantity of active material calculated to produce the desired therapeutic effect, in association with any suitable pharmaceutical excipient or excipients.

The recitation herein of numerical ranges by endpoints is intended to include all numbers subsumed within that range (e.g., a recitation of 1 to 5 includes 1, 1.5, 2, 2.75, 3, 3.80, 4, and 5).

Other features and advantages of the invention will be apparent from the following Detailed Description and from the claims.

DETAILED DESCRIPTION OF THE INVENTION

Figure 1:
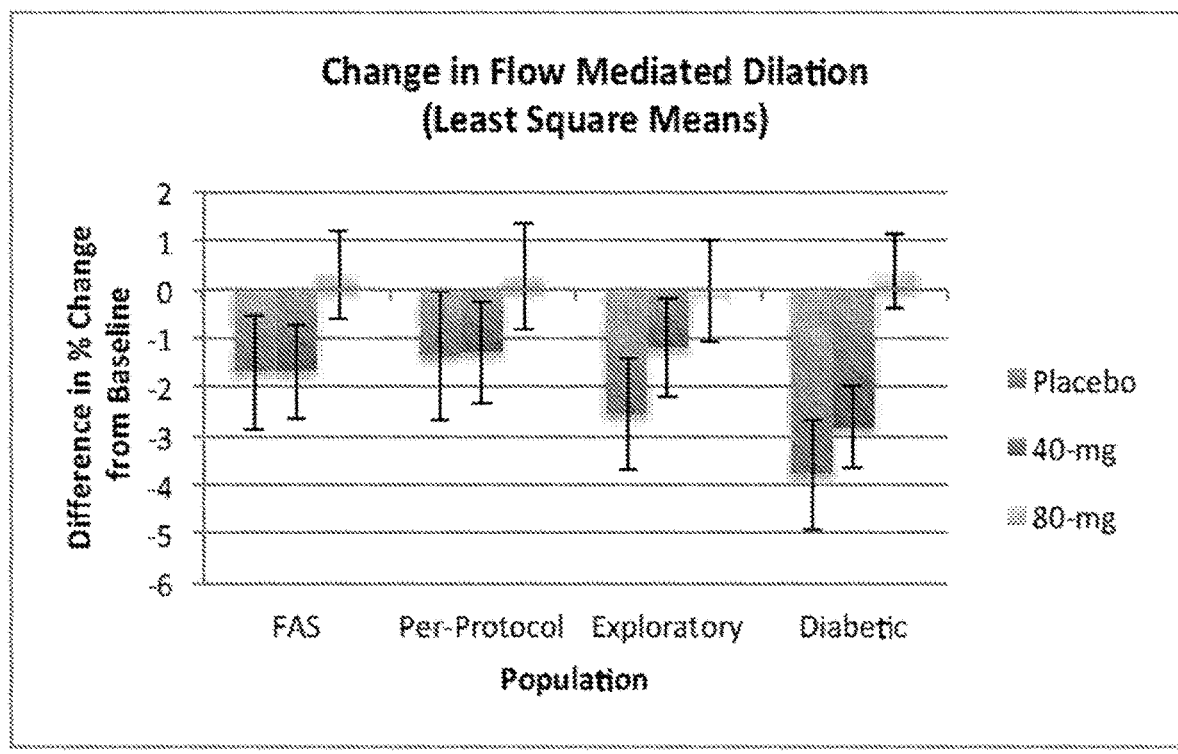
FIG. 1 is a graph showing flow mediated dilation (FMD) results for PAD patients at baseline and after 10 weeks of receiving placebo, 40 mg of an immediate release formulation of sodium nitrite (TV1001) twice daily (BID), or 80 mg TV1001 BID. The results are presented in adjusted least square means and as the difference in percentage change from baseline FMD.

We have discovered that inorganic nitrite (e.g., sodium nitrite ($NaNO_2$)) can be used to effectively treat both pain and symptoms associated with microvascular disease in a patient (e.g., a human). In particular, administration of inorganic nitrite at relatively low doses (e.g., about 5 mg to about 50 mg of inorganic nitrite twice daily) significantly reduces pain, while administration of inorganic nitrite at relatively high doses (e.g., 60 mg to about 100 mg of inorganic nitrite twice daily) treats symptoms associated with microvascular disease, such as nitric oxide availability, physical function, and motor neuron activity. Additionally, administration of about 60 mg to about 100 mg of inorganic nitrite twice daily (e.g., about 80 mg twice daily) improves nerve conduction velocity in patients identified as being in need of improved nerve conduction velocity (e.g., patients having a microvascular disease, such as diabetic neuropathy, peripheral artery disease, scleroderma, Raynaud's disease, cerebral autosomal dominant arteriopathy with sub-cortical infarcts and leukoencephalopathy, thrombotic microangiopathy, or thromboangiitis obliterans). In particular, patients can be identified as being in need of improved nerve conduction velocity using a monofilament prior to administration of the inorganic nitrite.

For example, the methods featuring the administration of inorganic nitrite can be used to reduce pain, such as chronic pain, in patients with microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans). Additionally, inorganic nitrite can be used to treat or reduce neuropathic pain (e.g., diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathy, mono-neuropathies, and central pain syndrome).

Inorganic nitrite (e.g., sodium nitrite ($NaNO_2$)) can also be used to improve nerve conduction velocity in a patient (e.g, a patient identified as being in need of improved nerve conduction velocity). In particular, administration of inorganic nitrite can improve nerve conduction velocity in patients with microvascular diseases, such as peripheral artery disease, diabetic neuropathy, scleroderma, Raynaud's disease, cerebral autosomal dominant arteriopathy with sub-cortical infarcts and leukoencephalopathy, thrombotic microangiopathy, and thromboangiitis obliterans. Additionally, these patients may not have pain associated with a microvascular disease.

Inorganic Nitrite

The compositions of the invention include inorganic nitrite, e.g., a salt or ester of nitrous acid ($HNO_2$), or a pharmaceutically acceptable salt thereof. In particular, inorganic nitrite, such as $NaNO_2$, $KNO_2$, or $Ca(NO_2)_2$, can be used to reduce pain in a patient, e.g., a patient that has a microvascular disease, or to treat symptoms of microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, and thromboangiitis obliterans). Inorganic nitrite, such as $NaNO_2$, $KNO_2$, or $Ca(NO_2)_2$, can also be used to improve nerve conduction velocity in a patient (e.g., a patient with a microvascular disease, such as diabetic neuropathy or peripheral artery disease) identified as being in need of improved nerve conduction velocity, such as by increasing nerve conduction velocity in the patient.

Given the results described herein, the treatment methods are not limited to administration of a particular form of inorganic nitrite. Nitrite salts that can be used in the methods include, without limitation, salts of alkali metals, e.g., sodium, potassium; salts of alkaline earth metals, e.g., calcium, magnesium, and barium; and salts of organic bases, e.g., amine bases and inorganic bases. Compounds that can be used in the methods featuring inorganic nitrite also include all isotopes of atoms occurring in the intermediate or final compounds. Isotopes include those atoms having the same atomic number but different mass numbers. For example, isotopes of hydrogen include tritium and deuterium. Inorganic nitrite compounds are also meant to include solvated (e.g., hydrated) forms. Nitrite has the chemical formula $NO_2^-$ and may exist as an ion in water. Sodium nitrite has the chemical formula $NaNO_2$ and typically dissolves in water to form the sodium ion $Na^+$ and the nitrite ion $NO_2^-$. Exemplary nitrite compounds are described in WO 2008/105730, hereby incorporated by reference in its entirety.

Representative inorganic nitrite compounds that can be used according to the methods for treating pain and/or symptoms of microvascular disease include ammonium nitrite ($NH_4NO_2$), barium nitrite ($Ba(NO_2)_2$; e.g., anhydrous barium nitrite or barium nitrite monohydrate), calcium nitrite ($Ca(NO_2)_2$; e.g., anhydrous calcium nitrite or calcium nitrite monohydrate), cesium nitrite ($CsNO_2$), cobalt(II) nitrite ($Co(NO_2)_2$), cobalt(III) potassium nitrite ($CoK_3(NO_2)_6$; e.g., cobalt(III) potassium nitrite sesquihydrate), lithium nitrite ($LiNO_2$; e.g., anhydrous lithium nitrite or lithium nitrite monohydrate), magnesium nitrite ($MgNO_2$; e.g., magnesium nitrite trihydrate), postassium nitrite ($KNO_2$), rubidium nitrite ($RbNO_2$), silver(I) nitrite ($AgNO_2$), strontium nitrite ($Sr(NO_2)_2$), and zinc nitrite ($Zn(NO_2)_2$).

Inorganic nitrite compounds that are useful in the methods of treating pain and/or microvascular disease can be prepared in a variety of ways known to one of ordinary skill in the art of chemical synthesis. Methods for preparing nitrite salts are well known in the art and a wide range of precursors and nitrite salts are readily available commercially. Nitrites of the alkali and alkaline earth metals can be synthesized by reacting a mixture of nitrogen monoxide (NO) and nitrogen dioxide ($NO_2$) with a corresponding metal hydroxide solution, as well as through the thermal decomposition of the corresponding nitrate. Other nitrites are available through the reduction of the corresponding nitrates.

Suitable pharmaceutically acceptable salts for use in the methods of treating pain and/or microvascular disease include, for example, sodium nitrite, potassium nitrite, or calcium nitrite. Still other exemplary salts are found in Remington's Pharmaceutical Sciences, 17th ed., Mack Publishing Company, Easton, Pa., 1985, p. 1418, Berge et al., *J. Pharmaceutical Sciences* 66:1-19, 1977 and *Pharmaceutical Salts: Properties, Selection, and Use*, (Eds. P. H. Stahl and C. G. Wermuth), Wiley-VCH, 2008, each of which is incorporated herein by reference in its entirety.

Pharmaceutical Compositions

Inorganic nitrite, e.g., a salt of nitrous acid ($HNO_2$) such as $NaNO_2$, or a pharmaceutically acceptable salt can be administered in the form of pharmaceutical compositions to reduce pain and to treat the symptoms of microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans) or to improve nerve conduction velocity in a patient in need thereof. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration. In particular, the inorganic nitrite is administered in a pharmaceutical composition as described in U.S. patent application Ser. No. 12/904,791, hereby incorporated by reference in its entirety.

Pharmaceutical compositions of inorganic nitrite useful in the methods of treating pain and microvascular disease or the methods of improving nerve conduction velocity can contain one or more pharmaceutically acceptable carriers. In making a pharmaceutical composition for use in the methods, the inorganic nitrite, pharmaceutically acceptable salt, solvate, or prodrug thereof is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents featuring inorganic nitrite (e.g., sodium nitrite) can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, $22^{nd}$ Ed., Allen (2012), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents;

emulsifying and suspending agents; preserving agents such as methyl- and propylhydroxy-benzoates; sweetening agents; and flavoring agents. Other exemplary excipients are described in *Handbook of Pharmaceutical Excipients, 6th* Edition, Rowe et al., Eds., *Pharmaceutical Press* (2009).

The compositions useful in the methods can be formulated in a unit dosage form, each dosage containing, e.g., 5 to 100 mg of inorganic nitrite (e.g., sodium nitrite). For example, the dosages can contain about 10 mg to about 50 mg, from about 15 mg to about 40 mg, from about 5 mg to about 20 mg, from about 5 mg to about 10 mg, from about 10 mg to about 20 mg, from about 5 mg to about 15 mg, from about 20 mg to about 40 mg, from about 20 mg to about 50 mg; from about 30 mg to about 40 mg, from about 30 mg to about 50 mg, from about 10 mg to about 30 mg, from about 70 mg to about 100 mg, from about 60 mg to about 80 mg, from about 80 mg to about 100 mg, from about 60 mg to about 90 mg, or from about 70 mg to about 85 mg of inorganic nitrite (e.g., sodium nitrite). For preparing solid compositions, such as tablets, the inorganic nitrite is mixed with one or more pharmaceutical excipients to form a solid bulk formulation composition containing a homogeneous mixture of a compound of the present invention. When referring to these bulk formulation compositions as homogeneous, the inorganic nitrite is typically dispersed evenly throughout the composition so that the composition can be readily subdivided into equally effective unit dosage forms such as tablets and capsules. This solid bulk formulation is then subdivided into unit dosage forms of the type described above.

Coatings

The pharmaceutical compositions of inorganic nitrite (e.g., $NaNO_2$) useful in the methods can be formulated for oral delivery. For instance, tablets or capsules of the present invention can be coated or otherwise compounded to provide a dosage form affording the advantage of delayed or extended release. The coating may be adapted to release the inorganic nitrite in a predetermined pattern (e.g., in order to achieve a controlled release formulation). Alternatively, the coating may not be adapted to release the inorganic nitrite or a pharmaceutically acceptable salt thereof until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")).

Exemplary enteric coatings that can be used in the pharmaceutical compositions including inorganic nitrite include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule of inorganic nitrite can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. When an enteric coating is used, desirably, a substantial amount of the drug is released in the lower gastrointestinal tract. In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Formulations for Colonic Drug Release

Colon-targeted drug delivery systems can be used in the methods featuring inorganic nitrite (e.g., $NaNO_2$). Exemplary approaches include, but are not limited to:

(a) covalent linkage of the drug with the carrier to form a prodrug that is stable in the stomach and small intestine and releases the drug in the large intestine upon enzymatic transformation by the intestinal microflora; examples of these prodrugs include azo-conjugates, cyclodextrin-conjugates, glycoside-conjugates, glucuronate conjugates, dextran-conjugates, polypeptide and polymeric conjugates;

(b) approaches to deliver intact molecule to the colon, such as coating with pH-sensitive polymers to release the drug at neutral to alkaline pH, or coating with biodegradable polymers which release the drug upon degradation by the bacteria in the colon;

(c) embedding the drug in biodegradable matrices and hydrogels which release the drug in response to the pH or biodegradation;

(d) time released systems where once the multicoated formulation passes the stomach, the drug is released after a lag time of 3-5 hrs which is equivalent to the transit time of the small intestine;

(e) using redox-sensitive polymers where a combination of azo and disulfide polymers, provide drug release in response to the redox potential of the colon;

(f) using bioadhesive polymers which selectively adhere to the colonic mucosa slowly releasing the drug; and (g) osmotic controlled drug delivery where the drug is released through semi-permeable membrane due to osmotic pressure.

Routes of Administration

Inorganic nitrite (e.g., $NaNO_2$) may be administered to a patient, such as a patient with pain and/or a microvascular disease or a patient in need of improved nerve conduction velocity, in a variety of forms depending on the selected route of administration, as will be understood by those skilled in the art and as relating to the particular disease or condition to be treated. The compositions used in the methods of reducing pain and/or treating a microvascular disease and in the methods of improving nerve conduction velocity may be administered, for example, by topical, enteral, or parenteral applications. Topical applications include but are not limited to epicutaneous, inhalation, enema, eye drops, ear drops, and applications through mucous membranes in the body. Enteral applications include oral administration, rectal administration, vaginal administration, and gastric feeding tubes. Parenteral administration includes intravenous, intraarterial, intracapsular, intraorbital, intracardiac, intradermal, transtracheal, subcuticular, intraarticular, subcapsular, subarachnoid, intraspinal, epidural, intrastemal, intraperitoneal, subcutaneous, intramuscular, transepithelial, nasal, intrapulmonary, intrathecal, rectal, and topical modes of administration. Parenteral administration may be by continuous infusion over a selected period of time.

For intravenous or intrathecal delivery or direct injection, the composition including inorganic nitrite must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating, such as lecithin, by maintenance of required particle size in the case of dispersion, and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The choice of the route of administration will depend on whether a local or systemic effect is to be achieved using the composition including inorganic nitrite. For local effects, the composition can be formulated for topical administration and applied directly where its action is desired. For systemic, long term effects, the composition can be formulated for enteral administration and given via the digestive tract. For systemic, immediate, and/or short term effects, the composition can be formulated for parenteral administration and given by routes other than through the digestive tract.

Parenteral Administration

Parenteral depot systems composed of biodegradable polymers are also useful in the methods featuring inorganic nitrite. These systems are injected or implanted into the muscle or subcutaneous tissue to release the inorganic nitrite over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Dosing Regimens

Inorganic nitrite (e.g., sodium nitrite ($NaNO_2$)) can be administered to a patient suffering from pain (e.g., neuropathic pain, inflammatory pain, nociceptive pain, functional pain, musculo-skeletal pain, or central nervous system pain) in an amount sufficient to treat or reduce the symptoms of pain (e.g., discomfort, soreness, tightness, stiffness, fatigue, sleeplessness, weakened immune system, depression, anxiety, stress, irritability, or disability). Inorganic nitrite can also be administered to a patient with a microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans) in an amount sufficient to treat symptoms of microvascular disease. For example, inorganic nitrite can be administered to a patient having a microvascular disease for a first treatment period at a dose effective to treat or reduce pain, and then administered to the patient for a second treatment period at a dose effective to treat one or more symptoms of the microvascular disease (e.g., decreased nitric oxide availability, physical function, and/or motor neuron activity).

Inorganic nitrite (e.g., $NaNO_2$) can be administered to a patient for a first treatment period (e.g., of at least 6 weeks, 7 weeks, 8 weeks, 9 weeks, 10 weeks, 11 weeks, 12 weeks, 13 weeks, 14 weeks, or longer) to treat or reduce pain (e.g., neuropathic pain, inflammatory pain, nociceptive pain, functional pain, musculo-skeletal pain, or central nervous system pain). Exemplary doses of inorganic nitrite administered (such as daily, e.g. twice daily) during the first treatment period can be from about 5 mg to about 50 mg; about 5 mg to about 20 mg; about 5 mg to about 30 mg; about 5 mg to about 40 mg; about 5 mg to about 45 mg; about 10 mg to about 20 mg; about 10 mg to about 30 mg; about 10 mg to about 40 mg; about 10 mg to about 50 mg; about 15 mg to about 25 mg; about 15 mg to about 35 mg; about 15 mg to about 45 mg; about 20 mg to about 30 mg; about 20 mg to about 40 mg; about 20 mg to about 50 mg; about 25 mg to about 35 mg; about 25 mg to about 45 mg; about 25 mg to about 50 mg; about 30 mg to about 40 mg; about 30 mg to about 45 mg; about 30 mg to about 50 mg; about 35 mg to about 40 mg; about 35 mg to about 45 mg; about 35 mg to about 50 mg; about 40 mg to about 45 mg; or about 40 mg to about 50 mg. For instance, the amount of inorganic nitrite administered (e.g., twice daily) can be 5 mg, 10 mg, 15 mg, 20 mg, 25 mg, 30 mg, 35 mg, 40 mg, 45 mg, or 50 mg during the first treatment period.

Following the first treatment period, the amount of inorganic nitrite (e.g., $NaNO_2$) administered to the patient can be increased during a second treatment period (e.g., of at least 6 weeks, at least 7 weeks, at least 8 weeks, at least 9 weeks, at least 10 weeks, at least 11 weeks, at least 12 weeks, at least 13 weeks, at least 14 weeks, or longer) to treat a microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans). Exemplary doses of inorganic nitrite administered (such as daily, e.g. twice daily) during the second treatment period can be from about 60 mg to about 100 mg; about 60 mg to about 70 mg; about 60 mg to about 80 mg; about 60 mg to about 90 mg; about 65 mg to about 75 mg; about 65 mg to about 85 mg; about 65 mg to about 95 mg; about 70 mg to about 80 mg; about 70 mg to about 90 mg; about 70 mg to about 100 mg; about 75 mg to about 85 mg; about 75 mg to about 90 mg; about 75 mg to about 100 mg; about 80 mg to about 90 mg; about 80 mg to about 95 mg; about 80 mg to about 100 mg; about 90 mg to about 100 mg; or about 95 mg to about 100 mg of inorganic nitrite. For instance, the amount of inorganic nitrite administered (e.g., twice daily) can be, e.g., 60 mg, 65 mg, 70 mg, 75 mg, 80 mg, 85 mg, 90 mg, 95 mg, or 100 mg during the second treatment period.

The methods also include administering inorganic nitrite (e.g., $NaNO_2$) for a first treatment period and then a second treatment period at a dosage ratio to a patient, such as a patient with pain and/or a microvascular disease, in which the dosage administered during the first treatment period (e.g., to treat pain) is lower than the dosage administered during the second treatment period (e.g., to treat a microvascular disease). For example, the ratio of inorganic nitrite administered during the first treatment period to inorganic nitrite administered during the second treatment period is approximately 1:20, 1:18, 1:16, 1:14, 1:12, 1:10, 1:9, 1:8, 1:7, 3:20, 1:6, 3:16, 1:5, 3:14, 2:9, 1:4, 5:18, 2:7, 3:10, 5:16, 1:3, 7:20, 5:14, 3:8, 7:18, 2:5, 5:12, 3:7, 7:16, 4:9, 9:20, 1:2, 5:9, 9:16, 4:7, 7:12, 5:8, 9:14, 2:3, 5:7, 3:4, or 5:6.

Additionally, the methods can include administering an amount of inorganic nitrite (e.g., $NaNO_2$) for a first treatment period (e.g., to treat pain) that is a fractional percentage of the amount of inorganic nitrite administered during the second treatment period (e.g., to treat a microvascular disease) to a patient, such as a patient with a microvascular disease. For instance, the amount of inorganic nitrite administered during the first treatment period is approximately 5%, 6%, 7%, 8%, 10%, 11%, 13%, 14%, 15%, 17%, 19%, 20%, 21%, 22%, 25%, 28%, 29%, 30%, 31%, 33%, 35%, 36%, 38%, 39%, 40%, 42%, 43%, 44%, 45%, 50%, 56%, 57%, 58%, 63%, 64%, 67%, 71%, 75%, or 83% of the amount of inorganic nitrite administered during the second treatment period.

The amount of inorganic nitrite administered to the patient, such as a patient with pain and/or a microvascular disease, per dose can vary. For example, a subject can receive from about 10 μg/kg to about 2,000 μg/kg of inorganic nitrite (e.g., sodium nitrite). Exemplary dosage amounts of inorganic nitrite include about 20 to about 1000 μg/kg; about 50 to about 2000 μg/kg; about 100 to about 1500 μg/kg; about 50 μg/kg to about 500 μg/kg; about 10 μg/kg to about 250 μg/kg; about 100 μg/kg to about 1,000 μg/kg; about 500 μg/kg to about 1500 μg/kg; about 60 to about 1250 μg/kg; about 340 to about 750 μg/kg; or about 750 to about 1300 μg/kg. Exemplary dosages of inorganic nitrite can include about 16.5 μg/kg, about 20 μg/kg, about 30 μg/kg, about 50 μg/kg, about 62.5 μg/kg, about 100 μg/kg, about 165 μg/kg, about 200 μg/kg, about 500 μg/kg, about 625 μg/kg, about 750 μg/kg, about 1000 μg/kg, about 1250 μg/kg, about 1500 μg/kg, about 1750 μg/kg, or about 2000 μg/kg. Typically, the amount of inorganic nitrite contained within a single dose will be an amount that is effective to treat a condition (e.g., pain and/or a microvascular disease) as described herein without inducing significant toxicity.

Inorganic nitrite (such as sodium nitrite) can be provided in either a single or multiple dosage regimens. Dosages of inorganic nitrite (e.g., sodium nitrite) can be administered, e.g., hourly, bihourly, daily, twice daily, twice a week, three times a week, four times a week, five times a week, six times a week, weekly, biweekly, monthly, bimonthly, or yearly. Additionally, dosages can be administered, e.g., twice, three times, four times, five times, six times, seven times, eight times, nine times, 10 times, 11 times, or 12 times per day. In particular, the dosing regimen is twice daily. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s), or even for the remaining lifespan of the patient with pain and/or microvascular disease.

The dosage of inorganic nitrite (e.g., sodium nitrite) administered to a patient with pain, such as chronic pain, can be adjusted based on whether the patient exhibits a reduction in pain after treatment with the inorganic nitrite. For instance, a patient with a microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans) can exhibit a reduction in pain after administration of inorganic nitrite at a lower dose (e.g., about 5 mg to about 50 mg twice daily) for a first treatment period (e.g., at least 6 weeks, least 7 weeks, at least 8 weeks, at least 9 weeks, at least 10 weeks, at least 11 weeks, at least 12 weeks, at least 13 weeks, at least 14 weeks, or longer). The reduction in pain can include a decrease in pain intensity, frequency, duration, and/or improvements in quality of life, which can be determined by, e.g., performing a Brief Pain Inventory, a Neuropathic Pain Symptom Inventory, and/or a McGill Pain Questionnaire.

When the patient with a microvascular disease exhibits a reduction in pain, the dose of inorganic nitrite (e.g., sodium nitrite) can then be increased to treat symptoms of microvascular disease, such as decreased nitric oxide availability, physical function, and/or motor neuron activity. In particular, about 5 mg to about 50 mg of inorganic nitrite can be administered twice daily for a first treatment period (e.g., at least 6 weeks, least 7 weeks, at least 8 weeks, at least 9 weeks, at least 10 weeks, at least 11 weeks, at least 12 weeks, at least 13 weeks, at least 14 weeks, or longer) until the patient exhibits a reduction in pain, then about 60 mg to about 100 mg of inorganic nitrite can be administered twice daily for a second treatment period to treat one or more symptoms of microvascular disease. Alternatively, when administration of inorganic nitrite (e.g., about 5 mg to about 50 mg of inorganic nitrite twice daily) does not result in a reduction in pain, the first treatment period can be extended (e.g., for 1 week, 2 weeks, 3 weeks 4 weeks, 5 weeks, 6 weeks, 7 weeks, 8 weeks, or more) or the dose and/or frequency of inorganic nitrite administration can be changed in order to determine the amount of inorganic nitrite that results in a reduction in pain.

For a patient with a microvascular disease (e.g., peripheral artery disease, diabetic neuropathy, scleroderma, Raynaud's disease, cerebral autosomal dominant arteriopathy with sub-cortical infarcts and leukoencephalopathy, thrombotic microangiopathy, or thromboangiitis obliterans), the dosage of inorganic nitrite (e.g., sodium nitrite) administered during the second treatment period (e.g., about 60 mg to about 100 mg twice daily, such as 80 mg twice daily) can also be adjusted based on whether the patient exhibits an improvement in one or more symptoms of microvascular disease (e.g., decreased nitric oxide availability, physical function, and/or motor neuron activity relative to a healthy subject). When administration of inorganic nitrite (e.g., about 60 mg to about 100 mg twice daily, such as 80 mg twice daily) does not result in an improvement in one or more symptoms of microvascular disease, the second treatment period can be extended (e.g., for 1 week, 2 weeks, 3 weeks 4 weeks, 5 weeks, 6 weeks, 7 weeks, 8 weeks, or more) or the dose and/or frequency of inorganic nitrite administration can be changed in order to determine the amount of inorganic nitrite that results in an improvement in one or more symptoms of a microvascular disease.

Additionally, inorganic nitrite (e.g., sodium nitrite ($NaNO_2$)) can be administered to a patient suffering from reduced nerve conduction velocity (e.g, a patient identified as being in need of improved nerve conduction velocity) to improve nerve conduction velocity in the patient. For example, a patient that can be administered inorganic nitrite to improve nerve conduction velocity can have a microvascular disorder, such as diabetic neuropathy, peripheral artery disease, scleroderma, Raynaud's disease, cerebral autosomal dominant arteriopathy with sub-cortical infarcts and leukoencephalopathy, thrombotic microangiopathy, and thromboangiitis obliterans. In particular, the patient can be a patient with diabetic neuropathy or peripheral artery disease. Thus, inorganic nitrite can be administered to a patient identified as being in need of improved nerve conduction velocity at a dosage that increases the nerve conduction velocity of the patient.

For example, inorganic nitrite (e.g., sodium nitrite ($NaNO_2$)) can be administered at a dosage of about 60 mg to about 100 mg twice daily (e.g., about 80 mg twice daily) to a patient identified as being in need of improved nerve conduction velocity (e.g., a patient with a microvascular disease, such as diabetic neuropathy or peripheral artery disease) for a treatment period sufficient to improve nerve conduction velocity in the patient. The treatment period can be, e.g., at least 6 weeks, 7 weeks, 8 weeks, 9 weeks, 10 weeks, 11 weeks, 12 weeks, 13 weeks, 14 weeks, 15 weeks, or 16 weeks or longer. Exemplary doses of inorganic nitrite administered daily (e.g., twice daily) to improve nerve conduction velocity can be from about 60 mg to about 100 mg; about 60 mg to about 70 mg; about 60 mg to about 80 mg; about 60 mg to about 90 mg; about 65 mg to about 75 mg; about 65 mg to about 85 mg; about 65 mg to about 95 mg; about 70 mg to about 80 mg; about 70 mg to about 90 mg; about 70 mg to about 100 mg; about 75 mg to about 85 mg; about 75 mg to about 90 mg; about 75 mg to about 100 mg; about 80 mg to about 90 mg; about 80 mg to about 95 mg; about 80 mg to about 100 mg; about 90 mg to about 100 mg; or about 95 mg to about 100 mg of inorganic nitrite (e.g., sodium nitrite ($NaNO_2$)). For instance, the amount of inorganic nitrite administered daily (e.g., twice daily) can be, e.g., 60 mg, 65 mg, 70 mg, 75 mg, 80 mg, 85 mg, 90 mg, 95 mg, or 100 mg to improve nerve conduction velocity in a patient in need thereof (e.g., a patient with a microvascular disease, such as diabetic neuropathy or peripheral artery disease).

The dosage of inorganic nitrite (e.g., sodium nitrite ($NaNO_2$)) administered to a patient in need of improved nerve conduction velocity, such as patient with a microvascular disease (e.g., diabetic neuropathy), can be adjusted based on whether the patient exhibits an improvement in nerve conduction velocity (e.g., an increase in nerve conduction velocity relative to prior to administration of the sodium nitrite). For example, the dosage can be increased and/or the treatment period may be extended by, e.g., at least 6 weeks, 7 weeks, 8 weeks, 9 weeks, 10 weeks, 11 weeks, 12 weeks, 13 weeks, 14 weeks, 15 weeks, or 16 weeks or longer, until the patient exhibits an improvement in nerve conduction velocity. Improvements in nerve conduction velocity can be determined over the treatment period by, e.g., performing a nerve conduction velocity test. In particular, a nerve conduction velocity test may be performed by, e.g., attaching two electrode's to a patient's skin over a test nerve, administering an electrical impulse through one electrode to stimulate the nerve, recording the electrical impulse through the nerve at the second electrode, and determining the time difference between stimulation from the first to second electrode (e.g., in m/s).

After administration of inorganic nitrite (e.g., about 60 mg to about 100 mg of inorganic nitrite twice daily, such as 70 mg or 80 mg of inorganic nitrite twice daily) to the patient, the patient can exhibit an increase in nerve conduction velocity of, e.g. about 1 m/s, about 1.5 m/s, about 2 m/s, about 2.5 m/s, about 3 m/s, about 3.5 m/s, about 4 m/s, about 4.5 m/s, about 5 m/s, about 5.5 m/s, about 6 m/s, or about 6.5 m/s or more relative to the nerve conduction velocity of the patient prior to administration of the inorganic nitrite. A sensory test may be performed to assess improvements in nerve conduction velocity, such as by placing a monofilament on the patient's skin (e.g., on the patient's feet) to assess the patient's ability to sense the monofilament. For example, the patient exhibits an increased ability to sense the monofilament after administration of the inorganic nitrite (e.g., about 60 mg to about 100 mg of inorganic nitrite twice daily, such as about 80 mg twice daily) relative to the ability of the patient to sense the monofilament prior to administration of the inorganic nitrite.

Methods of Treatment

Provided herein are methods for treating or reducing pain in a patient (e.g., a human) and for treating a patient with a microvascular disease, (e.g., peripheral artery disease, diabetic neuropathy, scleroderma, Raynaud's disease, Cerebral Autosomal Dominant Arteriopathy with Sub-cortical Infarcts and Leukoencephalopathy, thrombotic microangiopathy, and Thromboangiitis Obliterans). For instance, patients experiencing pain can be treated by the methods, such as by administering about 5 mg to about 50 mg of inorganic nitrite to the patient two times per day for, e.g., 6 weeks to 14 weeks, to reduce pain. A patient with a microvascular disease can also be treated with the methods, such as by administering about 5 mg to about 50 mg of inorganic nitrite to the patient two times per day for, e.g., 6 weeks to 14 weeks, to reduce pain, followed by administering about 60 mg to about 100 mg of inorganic nitrite (e.g., about 80 mg twice daily) to the patient two times per day for, e.g., 6 weeks to 14 weeks, to treat symptoms of microvascular disease. The invention also includes methods for improving nerve conduction velocity in a patient (e.g., a human), particularly a patient identified as being in need of improved nerve conduction velocity, such as a patient having a microvascular disease (e.g., diabetic neuropathy, peripheral artery disease, scleroderma, Raynaud's disease, cerebral autosomal dominant arteriopathy with sub-cortical infarcts and leukoencephalopathy, thrombotic microangiopathy, or thromboangiitis obliterans).

Pain

Pain is associated with a wide range of medical conditions. The present invention features inorganic nitrite for use in treating a patient (e.g., a human) with pain or conditions associated with pain. The methods of treatment are based, inter alia, on the inventor's discovery that inorganic nitrite (e.g., sodium nitrite) can be administered to treat patients with various forms of pain. Subjects treated using the methods can include subjects with acute pain, subacute pain, or chronic pain (e.g., pain that lasts longer than three to six months or pain that extends beyond the expected period of healing); or conditions associated with pain (e.g., postherpetic neuralgia, trigeminal neuralgia, phantom limb pain, carpal tunnel syndrome, sciatica, pudendal neuralgia, complex regional pain syndrome, or central pain syndrome, headaches, in particular, migraine, joint pain, backaches, sinus pain, muscle pain, nerve pain, and pain affecting specific parts of the body, such as shoulders, pelvis, and neck, and/or pain that is associated with lower back pain, arthritis, headache, fibromyalgia, shingles, or nerve damage).

Inorganic nitrite (e.g., sodium nitrite) is useful for the treatment or reduction of various forms of pain, whether acute or chronic. Exemplary conditions that may be associated with pain include, for example, soft tissue, joint, and bone inflammation and/or damage (e.g., acute trauma, osteoarthritis, or rheumatoid arthritis), myofascial pain syndromes (fibromyalgia), headaches (including cluster headache, migraine, and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures).

For example, the present invention provides methods of administering inorganic nitrite to alleviate neuropathic pain. Neuropathic pain can take a variety of forms depending on its origin and can be characterized as acute, subacute, or chronic depending on the duration. The pain may be described as being peripheral neuropathic if the initiating injury occurs as a result of a complete or partial transection of a nerve or trauma to a nerve plexus. Peripheral neuropathy can result from traumatic injuries, infections, metabolic disorders, diabetes, and/or exposure to toxins. Alternatively, neuropathic pain is described as being central neuropathic following a lesion to the central nervous system, such as a spinal cord injury or a cerebrovascular accident. Types of neuropathic pain that can be treated with inorganic nitrite (e.g., sodium nitrite) include, but are not limited to, diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, and central pain syndrome.

Additionally, methods for treating inflammatory pain by administering inorganic nitrite (e.g., sodium nitrite) are provided. Inflammatory pain is a form of pain caused by tissue injury or inflammation (e.g., in postoperative pain or rheumatoid arthritis). Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness associated with hypersensitivity to normally innocuous tactile stimuli), and/or spontaneous burning or shooting lancinating pain. In inflammatory pain, symptoms are apparent, at least initially, at the site of injury or inflamed tissues and typically accompany arthritis-associated pain, musculo-skeletal pain, and postoperative pain. The different types of pain may coexist or pain may be transformed from inflammatory to neuropathic during the natural course of the disease, as in post-herpetic neuralgia.

Inorganic nitrite (e.g., sodium nitrite) can also be used for the treatment, reduction, or prevention of musculo-skeletal pain (after trauma, infections, and exercise), pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, hereditary conditions, central nervous system pain, such as pain due to spinal cord or brain stem damage, cerebrovascular accidents, tumors, infections, demyelinating diseases including multiple sclerosis, low back pain, sciatica, and post-operative pain.

Microvascular Diseases

The present invention features the use of inorganic nitrite to treat a subject (e.g., a human) with a microvascular disease. For instance, inorganic nitrite (e.g., sodium nitrite) can be administered to treat patients with peripheral artery disease. In particular, patients with peripheral artery disease can be treated by administering about 5 mg to about 50 mg of inorganic nitrite (e.g., 40 mg of sodium nitrite) to the patient two times per day for 6 weeks to 14 weeks; and then administering about 60 mg to about 100 mg of inorganic nitrite (e.g., 80 mg of sodium nitrite) to the patient two times per day for 6 weeks to 14 weeks. The methods are useful for treating symptoms of peripheral artery disease, such as intermittent claudication, often described by patients as a cramping, aching, or fatigue sensation in the calf muscles of the legs that occurs during physical activity; limited exercise tolerance; coldness or changes in skin color of the lower extremities; hair loss or slower hair growth on your feet and legs; and a weak pulse in your feet and legs.

Likewise, inorganic nitrite (e.g., sodium nitrite) can be administered to treat patients having diabetic neuropathy. For instance, patients with diabetic neuropathy can be treated by administering about 5 mg to about 50 mg of inorganic nitrite (e.g., 40 mg of sodium nitrite) to the patient two times per day for 6 weeks to 14 weeks; and then administering about 60 mg to about 100 mg of inorganic nitrite (e.g., 80 mg of sodium nitrite) to the patient two times per day for 6 weeks to 14 weeks. In particular, the methods are useful for treating symptoms of diabetic neuropathy including, but not limited to, neuropathic pain, nerve damage, numbness, loss of balance, foot deformities, burning sensations, or tingling.

Moreover, inorganic nitrite (e.g., sodium nitrite) can be administered to treat patients with scleroderma. For example, patients with scleroderma can be treated by administering about 5 mg to about 50 mg of inorganic nitrite (e.g., 40 mg of sodium nitrite) to the patient two times per day for 6 weeks to 14 weeks; and then administering about 60 mg to about 100 mg of inorganic nitrite (e.g., 80 mg of sodium nitrite) to the patient two times per day for 6 weeks to 14 weeks. Thus, the methods are useful for treating symptoms of scleroderma including, but not limited to, hardening and tightening of patches of skin; numbness, pain, or color changes in the fingers or toes; acid reflux and digestive problems; ulcers or sores on fingertips; small red spots on the face and chest; opened blood vessels; puffy, painful, or swollen joints; muscle weakness; dry eyes or mouth; swelling of the hands and fingers; shortness of breath; and weight loss.

Inorganic nitrite (e.g., sodium nitrite) can also be administered, as described herein, to treat patients with Raynaud's syndrome. In particular, patients with Raynaud's syndrome can be treated by administering about 5 mg to about 50 mg of inorganic nitrite (e.g., 40 mg of sodium nitrite) to the patient two times per day for 6 weeks to 14 weeks; and then administering about 60 mg to about 100 mg of inorganic nitrite (e.g., 80 mg of sodium nitrite) to the patient two times per day for 6 weeks to 14 weeks. Accordingly, the methods are useful for treating symptoms of Raynaud's syndrome including, but not limited to, cold fingers or toes, color changes in your skin in response to cold or stress, numbness, or pain in the extremities.

For instance, inorganic nitrite can also be administered to treat patients with Cerebral Autosomal Dominant Arteriopathy with Sub-cortical Infarcts and Leukoencephalopathy (CADASIL). In particular, patients with CADASIL can be treated by administering about 5 mg to about 50 mg of inorganic nitrite (e.g., 40 mg of sodium nitrite) to the patient two times per day for 6 weeks to 14 weeks; and then administering about 60 mg to about 100 mg of inorganic nitrite (e.g., 80 mg of sodium nitrite) to the patient two times per day for 6 weeks to 14 weeks. Thus, the methods are useful for alleviating symptoms of CADASIL including, but not limited to, transient ischemic attacks, cerebral infarction, dementia, psychiatric disturbances, recurrent strokes, and migraine with aura.

Additionally, inorganic nitrite can be administered to treat patients with thrombotic microangiopathy. For example, patients with thrombotic microangiopathy can be treated by administering about 5 mg to about 50 mg of inorganic nitrite (e.g., 40 mg of sodium nitrite) to the patient two times per day for 6 weeks to 14 weeks; and then administering about 60 mg to about 100 mg of inorganic nitrite (e.g., 80 mg of sodium nitrite) to the patient two times per day for 6 weeks to 14 weeks. In particular, the methods are useful for treating symptoms of thrombotic microangiopathy including, but not limited to, fatigue, dizziness, shortness of breath, bruises, fever, microangiopathic hemolytic anemia, renal failure or complications, thrombocytopenia, neurological manifestations, and seizures.

Inorganic nitrite (e.g., sodium nitrite) can also be administered, as described herein, to treat patients with Thromboangiitis Obliterans. In particular, patients with Thromboangiitis Obliterans can be treated by administering about 5 mg to about 50 mg of inorganic nitrite (e.g., 40 mg of sodium nitrite) to the patient two times per day for 6 weeks to 14 weeks; and then administering about 60 mg to about 100 mg of inorganic nitrite (e.g., 80 mg of sodium nitrite) to the patient two times per day for 6 weeks to 14 weeks. Accordingly, the methods are useful for treating symptoms of Thromboangiitis Obliterans including, but not limited to, color changes in the fingers or toes; cold fingers or toes; pain in the hands and feet, particularly in exposure to cold or with emotional stress; intermittent claudication; or small painful ulcers on fingers or toes.

Nerve Conduction Velocity

The present invention features inorganic nitrite for use in treating a patient (e.g., a human) identified as being in need of improved nerve conduction velocity. The methods of treatment are based, inter alia, on the inventor's discovery that inorganic nitrite (e.g., sodium nitrite) can be administered to treat a patient in need of improved nerve conduction velocity, such as a patient identified as having reduced nerve conduction velocity relative to a healthy subject (e.g., a subject having a nerve conduction velocity of greater than about 45 m/s, such as about 50 m/s to about 60 m/s). For example, a patient identified as being in need of improved nerve conduction velocity may have a nerve conduction velocity of, e.g., less than 45 m/s, such as about 35 m/s, about 36 m/s, about 37 m/s, about 38 m/s, about 39 m/s, about 40 m/s, about 41 m/s, about 42 m/s, about 43 m/s, or about 44 m/s.

A patient (e.g., a patient having a microvascular disease, such as diabetic neuropathy, peripheral artery disease, scleroderma, Raynaud's disease, cerebral autosomal dominant arteriopathy with sub-cortical infarcts and leukoencephalopathy, thrombotic microangiopathy, or thromboangiitis obliterans) may be identified as being in need of improved nerve conduction velocity using a monofilament, such as in a monofilament test. For example, the bent monofilament (e.g., exerting a pressure of 10 grams) or unbent monofilament may be touched to different points on the sole of the patient's foot, and the patient will identify if they sense the monofilament. If the patient is unable to sense a bent monofilament, e.g., exerting 10 grams of pressure on the patient's foot, then the patient is identified as being in need of improved nerve conduction velocity. Inorganic nitrite (e.g., sodium nitrite) can then be administered to improve nerve conduction velocity in the patient. For example, administration of about 60 mg to about 100 mg of inorganic nitrite twice daily (e.g., about 70 mg or about 80 mg twice daily) can result in an improved ability of the patient to sense the monofilament. In particular, the patient exhibits an improved ability to sense the monofilament after administration of inorganic nitrite for a treatment period sufficient to improve nerve conduction velocity in the patient (e.g., a treatment period of at least 6 weeks, at least 7 weeks, at least 8 weeks, at least 9 weeks, at least 10 weeks, at least 11 weeks, at least 12 weeks, at least 13 weeks, or at least 14 weeks or longer).

Inorganic nitrite (e.g., sodium nitrite) can be administered to improve nerve conduction velocity in a patient (e.g., a human) with a microvascular disease. For example, administration of about 60 mg to about 100 mg of inorganic nitrite twice daily (e.g., about 70 mg or about 80 mg twice daily) can increase nerve conduction velocity in a patient with a microvascular disease, such as diabetic neuropathy, peripheral artery disease, scleroderma, Raynaud's disease, cerebral autosomal dominant arteriopathy with sub-cortical infarcts and leukoencephalopathy, thrombotic microangiopathy, or thromboangiitis obliterans. Thus, inorganic nitrite can be administered to a patient with any of these microvascular disease to increase the nerve conduction velocity (e.g., by about 1 m/s, about 1.5 m/s, about 2 m/s, about 2.5 m/s, about 3 m/s, about 3.5 m/s, about 4 m/s, about 4.5 m/s, about 5 m/s, about 5.5 m/s, about 6 m/s, or about 6.5 m/s or more relative to the patient prior to administration of the inorganic nitrite) of the patient. In particular, the patient having a microvascular disease exhibits an increase in nerve conduction velocity after administration of inorganic nitrite for a treatment period sufficient to improve nerve conduction velocity in the patient (e.g., a treatment period of at least 6 weeks, at least 7 weeks, at least 8 weeks, at least 9 weeks, at least 10 weeks, at least 11 weeks, at least 12 weeks, at least 13 weeks, or at least 14 weeks or longer).

Additionally, inorganic nitrite can be administered to a patient that exhibits deficits in balance and/or a reduced ability to sense pain relative to a healthy subject as a result of reduced nerve conduction velocity. For example, administration of about 60 mg to about 100 mg of inorganic nitrite twice daily (e.g., about 70 mg or about 80 mg twice daily) to a patient in need thereof (e.g., a patient identified as having deficits in balance and/or a reduced ability to sense pain) can increase the nerve conduction velocity (e.g., by about 1 m/s, about 1.5 m/s, about 2 m/s, about 2.5 m/s, about 3 m/s, about 3.5 m/s, about 4 m/s, about 4.5 m/s, about 5 m/s, about 5.5 m/s, about 6 m/s, or about 6.5 m/s or more relative to the patient prior to administration of the inorganic nitrite) of the patient. Moreover, the increase in nerve conduction velocity of the patient can be sustained through administration of the inorganic nitrite, e.g., for a treatment period of at least 6 weeks, at least 7 weeks, at least 8 weeks, at least 9 weeks, at least 10 weeks, at least 11 weeks, at least 12 weeks, at least 13 weeks, or at least 14 weeks or longer. For instance, the nerve conduction velocity increase to greater than 45 m/s and remains at greater than 45 m/s during treatment with the inorganic nitrite (e.g., sodium nitrite). Thus, the methods featuring the administration of inorganic nitrite are useful for improving a patient's ability to balance and sense pain by increasing the nerve conduction velocity of the patient.

Example 1. Clinical Studies of Sodium Nitrite

Sodium nitrite was investigated as a therapy for patients with microvascular disease, particularly patients with peripheral arterial disease (PAD) and patients with diabetic neuropathy. The overall goal of this dose-ranging study was to evaluate the efficacy of low and high doses of oral sodium nitrite (e.g., 40 mg sodium nitrite and 80 mg sodium nitrite, respectively) for treating pain and the pathophysiology associated with the microvascular diseases of PAD and diabetic neuropathy.

Two chronic dosing clinical trials were performed to study the safety and biological activity of an immediate release formulation of sodium nitrite (TV1001) in patients with PAD and a sustained release formulation of sodium nitrite (TV1001sr) in patients with diabetic neuropathy. The first trial included 55 human patients with PAD, in which 70% of patients also had diabetes. The PAD patients were randomized to receive one of the treatment regimens of placebo, 40 mg TV1001 twice daily (BID), or 80 mg TV1001 BID. The second trial included 30 patients with diabetic neuropathy. The diabetic neuropathy patients were randomized to receive one of the treatment regimens of placebo, 40 mg TV1001sr BID, or 80 mg TV1001sr BID. The trial with PAD patients was conducted for 10 weeks, and the trial with diabetic neuropathy patients was conducted for 12 weeks. Due to a manufacturing problem, the effective doses of TV1001sr were 35 mg and 70 mg during the trial period.

Example 2. Sodium Nitrite Decreases Pain in PAD Patient

Pain in PAD patients was assessed using a standardized pain scale score in which a higher score indicates less reported pain and a lower score indicates greater reported pain. Pain scores for the PAD patients were determined at baseline and after 10 weeks of receiving placebo, 40 mg TV1001 BID, or 80 mg TV1001 BID. Patients receiving 40 mg TV1001 BID had a pain scale score of 11.90 at day 70 of treatment, patients receiving 80 mg TV1001 BID had a pain scale score of −3.13 at day 70 of treatment, and patients receiving placebo had a pain scale score of −2.12 at day 70 of treatment (Table 1). Thus, patients receiving 40 mg TV1001 BID reported significantly less pain than the placebo group (p<0.05), whereas the 80 mg group reported a similar amount of pain as the placebo group. These results show that administration of the low dose (40 mg) of sodium nitrite twice daily resulted in a decrease in pain experienced by PAD patients in comparison to administration of the high dose (80 mg) of sodium nitrite twice daily or placebo.

Example 3. Sodium Nitrite Decreases Pain in Diabetic Neuropathy Patients

Pain in 28 patients with diabetic neuropathy during the clinical trial was evaluated using the Brief Pain Inventory (BPI), the Neuropathic Pain Symptom Inventory (NPSI), and the McGill Pain Index (MPI). The BPI is a questionnaire in which patients rate the severity of pain and degree of interference with function (see Cleeland & Ryan, *Ann. Acad. Med. Singapore*. 23(2):129-38, 1994; hereby incorporated by reference in its entirety). The different symptoms of neuropathic pain were evaluated using the NPSI (see Bouhassira et al. *Pain*. 108(3):248-57, 2004; hereby incorporated by reference in its entirety). The MPI was used to determine continuous and intermittent patterns of pain experienced by the patients (see Melzack. *Pain*. 1(3):277-99, 1975; hereby incorporated by reference in its entirety). A lower scores indicates less reported pain and a higher score indicates greater reported pain for the BPI, NPSI, and MPI.

Diabetic neuropathy subjects receiving 40 mg TV1001sr BID and 80 mg TV1001sr BID reported less pain after 12 weeks of treatment (visit 3 (V3)) based on the NPSI and the severity score of the BPI (Table 2). A comparison of V3 data for the NPSI to V1 data showed that subjects receiving 40 mg TV1001sr reported approximately 1.5 fold less pain and subjects receiving 80 mg TV1001sr reported approximately 2.6 fold less pain at V3 than subjects in the placebo group. The same trend was observed in the Severity Score of the BPI, in which subjects receiving 40 mg TV1001sr reported approximately 1.97 fold less pain and subjects receiving 80 mg TV1001sr reported approximately 2.34 fold less pain at V3 than subjects in the placebo group. For the MPI, patients receiving 40 mg TV1001sr reported slightly less pain than the placebo group, while patients receiving 80 mg TV1001sr reported very little reduction in pain using the MPI.

TABLE 1

Pain scale scores of PAD patients administered placebo, 40 mg TV1001 BID, or 80 mg TV1001 BID.

| | | TV1001 40 mg (N = 19) | TV1001 80 mg (N = 18) | TV1001 Combined (N = 37) | Placebo (N = 18) | P-value |
|---|---|---|---|---|---|---|
| Pain Scale Score: Visit 6 (Day 70)/Early Termination - Visit 1 (Day 0) | Least Squares Mean | 11.90 | −3.13 | 4.39 | −2.12 | |
| | Std. Error | 4.529 | 4.944 | 3.300 | 5.050 | |
| | TV1001 40 mg vs. TV1001 80 mg | | | | | 0.033 |
| | TV1001 40 mg vs. Placebo | | | | | 0.046 |
| | TV1001 80 mg vs. Placebo | | | | | 0.887 |
| | TV1001 40 mg and 80 mg combined vs. Placebo | | | | | 0.287 |

TABLE 2

Changes in Brief Pain Inventory (BPI), Neuropathic Pain Symptom Inventory Questionnaire (NPSI), and McGill Pain Index (MPI) scores of diabetic neuropathy patients administered placebo, 40 mg TV1001sr BID, or 80 mg TV1001sr BID from baseline (V1) to 12 weeks (V3).

| Brief Pain Inventory | | V1 | V2 Change from V1 | V3 Change from V1 | % Change of V3 to V1 | TV1001sr Fold Improvement Over Placebo |
|---|---|---|---|---|---|---|
| Severity Score | Placebo | 5.1 | −0.96 | −0.24 | 5.9% | |
| | 40 mg | 4.3 | −1.06 | −0.48 | 11.6% | 1.97 |
| | 80 mg | 5.9 | −0.54 | −0.84 | 13.6% | 2.34 |
| Interference Score | Placebo | 5.0 | −0.57 | −0.73 | 14.0% | |
| | 40 mg | 4.4 | −1.11 | −0.20 | 4.5% | −3.11 |
| | 80 mg | 6.4 | 0.62 | 0.77 | 10.94% | −1.28 |
| Neuropathic Pain Symptom Inventory | | | | | | |
| Total Score | Placebo | 47.4 | −8.44 | −4.00 | 8.4% | |
| | 40 mg | 34.7 | −4.71 | −4.43 | 12.7% | 1.51 |
| | 80 mg | 56.0 | −1.88 | −10.00 | 22.0% | 2.62 |
| McGill Pain Index | | | | | | |
| Total Score | Placebo | 5.1 | −1.4 | −1.5 | 29.4% | |
| | 40 mg | 3.9 | −0.7 | −1.4 | 35.9% | 1.22 |
| | 80 mg | 4.8 | 0.8 | −0.2 | 4.2% | −7.00 |
| Continuous Pain | Placebo | 5.0 | −1.9 | −1.8 | 36.0% | |
| | 40 mg | 3.7 | −0.2 | −1.7 | 48.6% | 1.35 |
| | 80 mg | 4.4 | 1.2 | −0.1 | 2.3% | −15.7 |
| Intermittent Pain | Placebo | 6.0 | −1.6 | −1.9 | 31.7% | |
| | 40 mg | 4.6 | −1.1 | −1.8 | 39.1% | 1.23 |
| | 80 mg | 5.9 | 0.7 | −0.6 | 10.2% | −3.11 |

Although all diabetic neuropathy subjects reported a decrease in pain in the Total Score section of the NPSI questionnaire, diabetic neuropathy subjects receiving 40 mg TV1001sr BID and 80 mg TV1001sr BID reported the greatest reduction in pain at V3 (Table 3). The 40 mg dose group reported significantly less pain than the 80 mg treatment group at baseline and throughout the study (ANOVA, df=2, F=4.38, p=0.02).

TABLE 3

Summary of Neuropathic Pain Symptom Inventory Questionnaire (NPSI) scores of diabetic neuropathy patients administered placebo, 40 mg TV1001sr BID, or 80 mg TV1001sr BID from baseline (V1) to 12 weeks (V3).

| | | | Visit 1 | Visit 2 | Visit 3 |
|---|---|---|---|---|---|
| NPSI Total | Placebo | Mean | 47.4 | 39.0 | 43.4 |
| | | S.D. | 25.7 | 24.4 | 25.3 |
| | | N | 9 | 9 | 9 |
| | 40 mg TV1001sr | Mean | 34.7 | 30.0 | 30.3 |
| | | S.D. | 22.2 | 22.7 | 26.2 |
| | | N | 7 | 7 | 7 |
| | 80 mg TV1001sr | Mean | 56.0 | 54.1 | 46.0 |
| | | S.D. | 18.0 | 16.2 | 23.9 |
| | | N | 8 | 8 | 8 |

Pain in diabetic neuropathy subjects receiving 40 mg TV1001sr BID and 80 mg TV1001sr BID was also assessed using the Total Severity and Total Interference scores of the BPI (Table 4). In both of the BPI sections, subjects receiving 40 mg TV1001sr BID reported significantly less pain at baseline (V1) and throughout the trial period as did the 80 mg dose group (ANOVA, Total Severity: F=3.39, p=0.04; Total Interference: F=4.82, p=0.01). For the Total Severity BPI scores, subjects receiving 40 mg TV1001sr BID and 80 mg TV1001sr also exhibited the greatest reported decrease in pain.

TABLE 4

Summary of Brief Pain Inventory (BPI) Total Severity and Total Interference scores of diabetic neuropathy patients administered placebo, 40 mg TV1001sr BID, or 80 mg TV1001sr BID from baseline (V1) to 12 weeks (V3).

| | | | Visit 1 | Visit 2 | Visit 3 |
|---|---|---|---|---|---|
| BPI Total Severity | Placebo | Mean | 5.1 | 4.1 | 4.8 |
| | | S.D. | 2.1 | 2.6 | 2.3 |
| | | N | 9 | 9 | 9 |
| | 40 mg TV1001sr | Mean | 4.3 | 3.2 | 3.8 |
| | | S.D. | 2.6 | 1.9 | 2.6 |
| | | N | 7 | 7 | 7 |
| | 80 mg TV1001sr | Mean | 5.9 | 5.4 | 5.1 |
| | | S.D. | 1.9 | 1.3 | 2.1 |
| | | N | 8 | 8 | 8 |
| BPI Total Interference | Placebo | Mean | 5.0 | 4.4 | 4.3 |
| | | S.D. | 3.4 | 3.0 | 4.0 |
| | | N | 9 | 9 | 9 |
| | 40 mg TV1001sr | Mean | 4.4 | 3.2 | 4.2 |
| | | S.D. | 2.4 | 2.6 | 2.6 |
| | | N | 7 | 7 | 7 |
| | 80 mg TV1001sr | Mean | 6.4 | 7.1 | 5.7 |
| | | S.D. | 2.3 | 1.6 | 2.1 |
| | | N | 8 | 8 | 8 |

Pain in diabetic neuropathy subjects receiving 40 mg TV1001sr BID and 80 mg TV1001sr BID was also assessed using the McGill Questionnaire Total Intermittent pain score, Total Continuous pain score, and Total pain score (Table 5). For the McGill Total score (ANOVA, F=3.67, p=0.03) and the Intermittent score (ANOVA, F=3.98, p=0.02), the 40 mg TV1001 subjects had significantly lower scores than the 80 mg group. Unlike the other pain questionnaires, the subjects treated with 80 mg TV1001sr reported very little reduction in pain as assessed with the MPI, well less than that reported by subjects in the placebo group.

TABLE 5

Summary of McGill Pain Index (MPI) scores of diabetic neuropathy patients administered placebo, 40 mg TV1001sr BID, or 80 mg TV1001sr BID from baseline (V1) to 12 weeks (V3).

|  |  |  | Visit 1 | Visit 2 | Visit 3 |
|---|---|---|---|---|---|
| McGill Total | Placebo (N = 9) | Mean | 5.1 | 3.7 | 3.6 |
|  |  | S.D. | 2.4 | 2.0 | 2.5 |
|  | 40 TV1001sr (N = 7) | Mean | 3.9 | 3.1 | 2.5 |
|  |  | S.D. | 2.4 | 1.9 | 2.4 |
|  | 80 TV1001sr (N = 8) | Mean | 4.8 | 5.6 | 4.6 |
|  |  | S.D. | 2.2 | 2.0 | 2.1 |
| McGill Continuous | Placebo (N = 9) | Mean | 5.0 | 3.1 | 3.2 |
|  |  | S.D. | 3.0 | 2.2 | 2.2 |
|  | 40 TV1001sr (N = 7) | Mean | 3.7 | 3.5 | 1.9 |
|  |  | S.D. | 2.5 | 3.5 | 2.2 |
|  | 80 TV1001sr (N = 8) | Mean | 4.4 | 5.6 | 4.3 |
|  |  | S.D. | 2.5 | 2.5 | 2.1 |
| McGill Intermittent | Placebo (N = 9) | Mean | 6.0 | 4.4 | 4.1 |
|  |  | S.D. | 2.9 | 2.7 | 3.6 |
|  | 40 TV1001sr (N = 7) | Mean | 4.6 | 3.5 | 2.8 |
|  |  | S.D. | 2.5 | 2.4 | 2.9 |
|  | 80 TV1001sr (N = 8) | Mean | 5.9 | 6.6 | 5.3 |
|  |  | S.D. | 3.0 | 2.2 | 2.4 |

Figure 3:
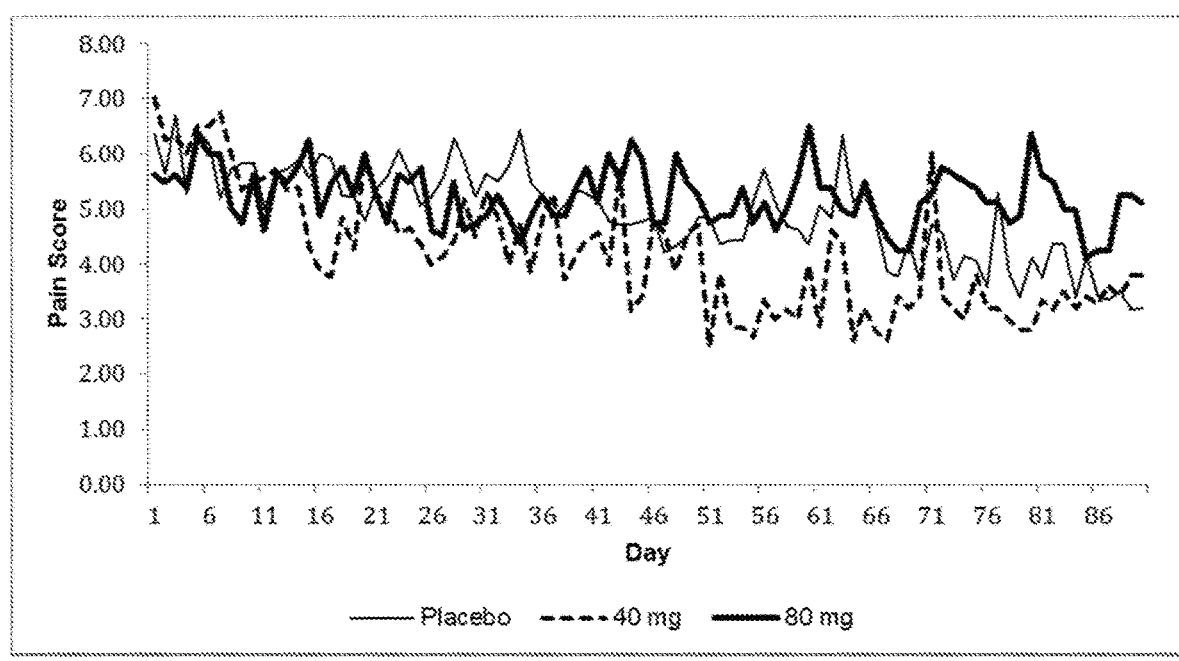
FIG. 3 is a graph showing daily pain logs for patients with diabetic neuropathy over 86 days of treatment with 40 mg TV1001sr BID, 80 mg TV1001sr BID, or placebo.

Diabetic neuropathy subjects receiving 40 mg TV1001sr BID, 80 mg TV1001sr BID, or placebo were also given a log book and instructed to record the level of pain experienced on each day at the time of treatment. Subjects in the 40 mg TV1001sr BID group reported a quicker reduction in pain and an overall greater reduction in pain than either the placebo or 80 mg TV1001sr BID groups (FIG. 3). When the means of the final visit were subtracted from the baseline value for each treatment group, the 40 mg TV1001sr BID treatment group reported the greatest reduction in pain, a mean drop of 4.0 (SD=4.3), while the placebo group reported a mean drop of 2.1 (SD=0.7). Very little change in pain perception was reported by subjects in the 80 mg TV1001sr BID treatment group, with a mean drop of only 0.5 (SD=1.4).

Example 4. Sodium Nitrite Improves Symptoms of Microvascular Disease

The biological activity of sodium nitrite was assessed by flow-mediated dilation (FMD) for PAD patients at baseline and after 10 weeks of receiving placebo, 40 mg TV1001 BID, or 80 mg TV1001 BID. FMD is a noninvasive method to measure endothelial dysfunction using, e.g., Brachial Artery Ultrasound Imagining (see Peretz et al. *BMC Cardiovasc. Disord.* 7:11, 2007; hereby incorporated by reference in its entirety). The Exploratory Group consisted of PAD patients that completed the protocol as instructed and took >70% of their medication. PAD patients receiving 80 mg TV1001 BID exhibited the most significant improvement in FMD for all groups from baseline (FIG. 1). In particular, there was a dose dependent improvement in FMD in the Exploratory Group with patients receiving 80 mg TV1001 BID exhibiting the greatest increase in FMD. Notably, diabetic PAD patients demonstrated a statistically significant improvement in FMD.

Figure 2:
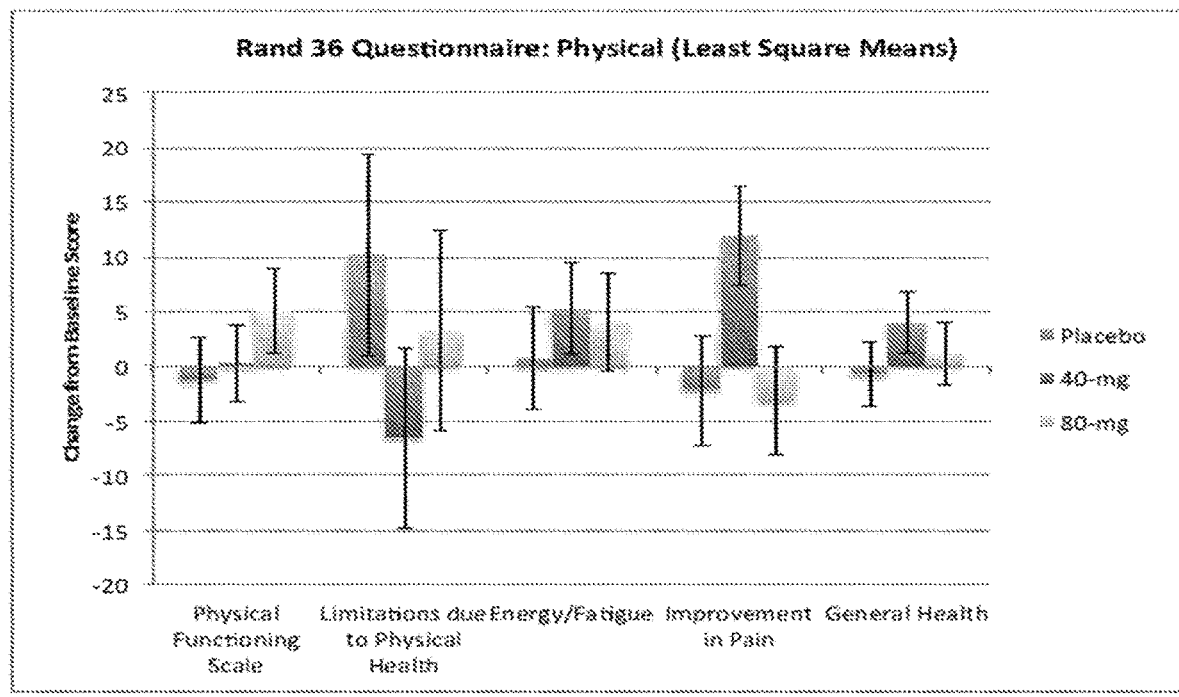
FIG. 2 is a graph showing RAND-36 Questionnaire results for PAD patients at baseline and after 10 weeks of receiving placebo, 40 mg TV1001 BID, or 80 mg TV1001 BID. Patients were evaluated in the RAND-36 Questionnaire categories of Physical Functioning, Limitations due to Physical Health, Energy/Fatigue, Improvements in Pain, and General Health.

The RAND-36 Questionnaire was used to assess changes in quality of life of PAD patients at baseline and after 10 weeks of receiving placebo, 40 mg TV1001 BID, or 80 mg TV1001 BID. The RAND-36 Questionnaire is a 36-item, patient-reported survey of patient health. PAD patients were evaluated in the RAND-36 Questionnaire categories of Physical Functioning, Limitations due to Physical Health, Energy/Fatigue, Improvements in Pain, and General Health (FIG. 2). For the Physical Functioning scale, patients receiving 80 mg TV1001 BID exhibited a greater change from the baseline score after 10 weeks of treatment relative to patients receiving 40 mg TV1001 BID or the patients receiving placebo. Thus, the 80 mg dose provided the greatest benefit in physical function of PAD patients.

For the RAND-36 Questionnaire, patients receiving 40 mg TV1001 BID and 80 mg TV1001 BID exhibited a similar increase in the change from baseline for the Energy/Fatigue score relative to patients receiving the placebo. Accordingly, both 40 mg TV1001 BID and 80 mg TV1001 BID appeared to improve levels of energy and fatigue in PAD patients. Additionally, patients receiving 40 mg TV1001 BID exhibited a greater improvement in pain relative to patients receiving 80 mg TV1001 BID or the placebo patients. These results corroborate that low dose (40 mg) sodium nitrite decreases pain in diabetic neuropathy patients, as is described in Example 3.

Figure 4:
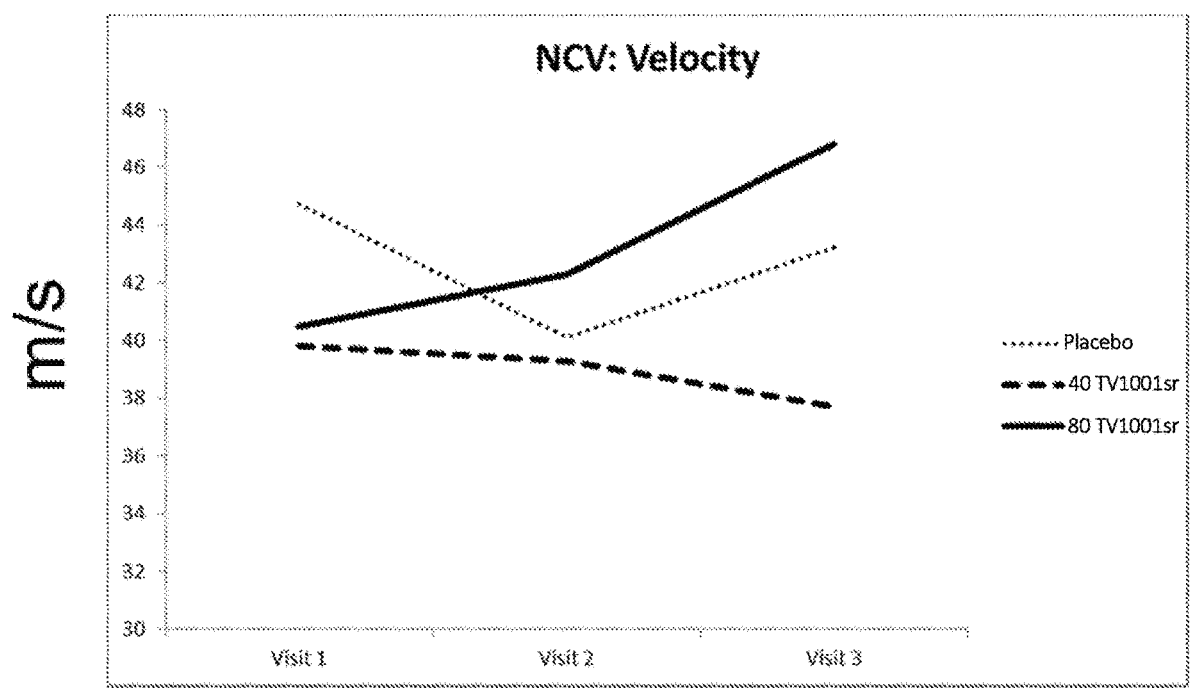
FIG. 4 is a graph showing nerve conduction velocity for patients with diabetic neuropathy at baseline (Visit 1) and after 10 weeks (Visit 3) of receiving 40 mg of a sustained release formulation of sodium nitrite (TV1001sr) BID, 80 mg TV1001sr BID, or placebo.

Example 5. Sodium Nitrite Improves Nerve Conduction Velocity in Diabetic Neuropathy Patients Nerve conduction velocity was also measured as a biological indicator of nerve health in patients with diabetic neuropathy receiving 40 mg TV1001sr BID, 80 mg TV1001sr BID, or placebo. For Visit 1, Visit 2, and Visit 3, three conduction measures were averaged and three velocity measures were averaged. Nerve conduction velocity improved in patients receiving 80 mg TV1001sr BID in comparison to patients receiving 40 mg TV1001sr BID or placebo (FIG. 4).

The nerve conduction velocity measures were also analyzed using an Analysis of Variance with one between-subjects factor (Group: both placebo groups combined, 40 mg TV1001sr BID, and 80 mg TV1001sr BID) and one within-subjects factor (Visit: Visit 1, Visit 2, and Visit 3). There were significant differences among the groups for the conduction measures, but not for the velocity measures. There was no significant effect for the Visit factor or for the Group by Visit interaction for either conduction or velocity. There was a significant effect for Group. Specifically, the velocity values for the 80 mg TV1001sr BID group were significantly higher than the values for the 40 mg TV1001sr BID group. Thus, administration of the high dose (80 mg) formulation of sodium nitrite twice daily resulted in a statistically significant improvement in nerve conduction velocity in patients with diabetic neuropathy over a treatment period of ten weeks.

There were no significant differences in Quantitative Sensory Testing at baseline among the groups, the average sensory conductance was higher for the 80 mg TV1001sr BID group than the placebo or 40 mg TV1001sr BID group, and average sensory velocity was lower for the 80 mg TV1001sr BID group (Table 6). Nerve sensory conductance showed very little change between baseline testing and Visits 1 and 2 for the placebo and 40 mg TV1001sr BID group, but trended toward decreasing for the 80 mg TV1001sr BID group (p=0.154). Similarly, nerve sensory velocity remained stable for the placebo and 40 mg TV1001sr BID group, but exhibited a trend towards increasing (p=0.116) with continued improvement for the 80 mg TV1001sr BID group.

TABLE 6

Efficacy analysis of Quantitative Sensory Testing (QST)
for diabetic neuropathy patients administered placebo,
40 mg TV1001sr BID, or 80 mg TV1001sr BID.

| | Treatment Group | | |
|---|---|---|---|
| | Placebo (n = 9) | TV1001sr 40 mg (n = 6) | TV1001sr 80 mg (n = 8) |
| Nerve Conductance | | | |
| Baseline: Mean (SD) | 3.9 (1.4) | 3.4 (0.7) | 6.0 (2.9) |
| Visit 2: Mean (SD) | 4.3 (1.8) | 3.1 (0.9) | 5.2 (3.0) |
| Visit 3: Mean (SD) | 3.5 (1.2) | 3.2 (0.6) | 4.2 (1.5) |
| Nerve Velocity | | | |
| Baseline: Mean (SD) | 44.7 (6.5) | 41.1 (4.3) | 39.4 (8.2) |
| Visit 2: Mean (SD) | 40.1 (5.3) | 39.3 (7.8) | 42.3 (10.7) |
| Visit 3: Mean (SD) | 43.2 (6.4) | 37.7 (3.2) | 46.8 (4.2) |

Example 6: Reduction in Headaches with Sustained Release Formulation of Sodium Nitrite All subjects in the placebo and 40 mg TV1001sr BID treatment group, and 7 of the 9 subjects in the 80 mg TV1001sr BID treatment group, reported at least one adverse event (AE). The total number of reported AEs was slightly higher for the placebo group, but not really different from those in the TV1001sr groups (Table 7). Importantly, headaches, which was the most common AE reported previously for an immediate release formulation of sodium nitrite were not reported by any subjects in the 40 mg TV1001sr BID treatment group and were reported by the same number of subjects in the 80 mg TV1001sr BID treatment group as in the placebo group (2 subjects each).

TABLE 7

Summary of adverse events for diabetic neuropathy patients administered placebo, 40 mg TV1001sr BID, or 80 mg TV1001sr BID.

| | Treatment | | |
|---|---|---|---|
| | Placebo (n = 9) | TV1001sr 40 mg (n = 8) | TV1001sr 80 mg (n = 9) |
| Number (%) of Subjects with at least one AE | 9 (100.0%) | 8 (100.0%) | 7 (77.8%) |
| Number of AEs | 29 | 23 | 23 |
| Number of SAEs | 2 | 5 | 2 |
| Numbers of AEs by Severity | | | |
| Mild | 23 | 14 | 17 |
| Moderate | 2 | 5 | 4 |
| Severe | 1 | 4 | 1 |
| Not Recorded | 3 | 0 | 1 |
| Number of AEs by Relationship to Study Drug | | | |
| Not Related | 24 | 19 | 19 |
| Possibly Related | 5 | 4 | 4 |
| Probably Related | 0 | 0 | 0 |
| AEs Appearing Related to Previous Exposure to Study Drug Dose | | | |
| Headache | 2 (22.2%) | 0 (0%) | 2 (22.2%) |
| Not Related | 1 (11.1%) | 0 (0%) | 0 (0%) |
| Possibly Related | 1 (11.1%) | 0 (0%) | 2 (22.2%) |
| Dizziness (incl. shakiness) | 2 (22.2%) | 2 (25%) | 2 (22.2%) |
| Not Related | 0 (0) | 1 (12.5%) | 1 (11.1%) |
| Possibly Related | 2 (22.2%) | 1 (12.5%) | 1 (11.1%) |

These results indicate that treatment with TV1001sr appears tolerable in patients with diabetic neuropathy and the use of the sustained release formulation seems to eliminate the headaches and dizziness noted in prior studies of an immediate release formulation. There was a trend across questionnaires that demonstrated a potential benefit, particularly of 40 mg TV1001sr BID, in reducing total pain at the end of the trial period compared to that at baseline. A trend toward improving nerve function was observed following treatment with 80 mg TV1001sr. Thus, these results demonstrates that TV1001sr eliminated headaches and dizziness.

Example 7. Summary of Clinical Studies Featuring Sodium Nitrite Administered Twice Daily Administration of low dose (40 mg) sodium nitrite twice daily resulted in a statistically significant reduction in pain for PAD and diabetic neuropathy patients, while administration of the high dose (80 mg) of sodium nitrite twice daily improved symptoms of microvascular disease in PAD and diabetic neuropathy patients. Additionally, administration of the sustained release formulation of sodium nitrite (TV1001sr) twice daily eliminated headaches and dizziness associated with TV1001.

Based on these results, an appropriate dosing schedule will be to treat a patient (e.g., a patient with PAD or diabetic neuropathy) that has chronic pain due to microvascular disease with about 5 mg to about 50 mg TV1001sr BID (e.g., 40 mg TV1001sr BID) for 6 weeks to 14 weeks (e.g., 10 weeks) to reduce pain. Then, the dosage of TV1001sr would be increased to about 60 mg to about 100 mg administered BID (e.g., 80 mg TV1001sr BID) to improve and maintain the biological response to sodium nitrite in patients with microvascular disease.

For diabetic neuropathy patients, Brief Pain Inventory (BPI), Neuropathic Pain Symptom Inventory Questionnaire (NPSI), and McGill Pain Index (MPI) scores in addition to daily pain logs indicated that treatment with 40 mg TV1001sr BID resulted in a reduction in pain. Pain was also reduced in diabetic neuropathy subjects receiving 80 mg TV1001sr BID as assessed by the NPSI and the BPI. Treatment with 80 mg TV1001sr BID also improved nerve function in diabetic neuropathy patients. These results indicate that administration of 80 mg TV1001sr BID may be preferred for long-term treatment of pain and to improve nerve function in patients with chronic pain and reduced nerve function, such as patients having diabetic neuropathy.

Other Embodiments

Various modifications and variations of the described methods will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. A method of improving nerve conduction velocity in a patient identified as being in need of improved nerve conduction velocity, the method comprising:
administering between 60 mg and 100 mg of inorganic nitrite or a pharmaceutically acceptable salt thereof twice daily to the patient for a treatment period sufficient to improve nerve conduction velocity in the patient.

2. The method of claim 1, further comprising monitoring whether there is an increase in nerve conduction velocity in the patient.

3. The method of claim 2, wherein the monitoring is performed by using a nerve conduction velocity test or a sensory test.

4. The method of claim 1, wherein there is an increase in nerve conduction velocity after administration of the inorganic nitrite or the pharmaceutically acceptable salt.

5. The method of claim 4, wherein the increase in nerve conduction velocity is one 1 m/s, 1.5 m/s, 2 m/s, 2.5 m/s, 3 m/s, 3.5 m/s, 4 m/s, 4.5 m/s, 5 m/s, 5.5 m/s, 6 m/s, 6.5 m/s or between 1 m/s and 7 m/s relative to the nerve conduction velocity of the patient prior to administration of the inorganic nitrite or the pharmaceutically acceptable salt.

6. The method of claim 1, wherein the patient exhibits an increased ability to sense a monofilament after administration of the inorganic nitrite or the pharmaceutically acceptable salt.

7. The method of claim 1, wherein the patient has a microvascular disease.

8. The method of claim 7, wherein the microvascular disease is selected from the group consisting of diabetic neuropathy, peripheral artery disease, scleroderma, Raynaud's disease, cerebral autosomal dominant arteriopathy with sub-cortical infarcts and leukoencephalopathy, thrombotic microangiopathy, and thromboangiitis obliterans.

9. The method of claim 8, further comprising determining whether the patient experiences an improvement in one or more symptoms of the microvascular disease.

10. The method of claim 9, wherein the patient experiences an improvement in one or more symptoms of the microvascular disease after administration of the inorganic nitrite or the pharmaceutically acceptable salt.

11. The method of claim 1, wherein the patient does not have pain associated with a microvascular disease.

12. The method of claim 1, wherein the inorganic nitrite one of is $NaNO_2$, $KNO_2$, or $Ca(NO_2)_2$.

13. The method of claim 1, wherein the inorganic nitrite is $NaNO_2$.

14. The method of claim 1, wherein the inorganic nitrite or the pharmaceutically acceptable salt thereof is administered in a tablet or a capsule.

15. The method of claim 14, wherein the inorganic nitrite or the pharmaceutically acceptable salt thereof is administered in a sustained release formulation.

16. The method of claim 1, wherein the inorganic nitrite or the pharmaceutically acceptable salt is administered with one or more pharmaceutically acceptable excipients.

17. The method of claim 1, wherein the treatment period is at least 6 weeks, at least 7 weeks, at least 8 weeks, at least 9 weeks, at least 10 weeks, at least 11 weeks, at least 12 weeks, at least 13 weeks, or at least 14 weeks or longer.

18. The method of claim 1, wherein the inorganic nitrite or the pharmaceutically acceptable salt thereof is administered twice daily in a dosage of between 70 mg to 90 mg.

19. The method of claim 18, wherein the inorganic nitrite or the pharmaceutically acceptable salt thereof is administered twice daily in a dosage of about 70 mg, about 75 mg, about 80 mg, 85 mg, or about 90 mg.

20. The method of claim 1, wherein the patient is a human.

* * * * *